(12) United States Patent
Yu et al.

(10) Patent No.: US 11,744,762 B2
(45) Date of Patent: Sep. 5, 2023

(54) GAIT ACTIVITY LEARNING ASSISTANCE SYSTEM AND THE APPLICATION METHOD THEREOF

(71) Applicant: NATIONAL YANG-MING UNIVERSITY, Taipei (TW)

(72) Inventors: Chung-Huang Yu, Taipei (TW); Fu-Cheng Wang, Taipei (TW); Po-Yin Chen, Taipei (TW); Hsiao-Kuan Wu, Taipei (TW); Yu-You Lin, Taipei (TW); Kai-Lin Wu, Taipei (TW)

(73) Assignee: National Yang Ming Chiao Tung University, Taipei (TW)

( * ) Notice: Subject to any disclaimer, the term of this patent is extended or adjusted under 35 U.S.C. 154(b) by 1091 days.

(21) Appl. No.: 16/420,617

(22) Filed: May 23, 2019

(65) Prior Publication Data

US 2020/0030176 A1    Jan. 30, 2020

(30) Foreign Application Priority Data

Jul. 27, 2018   (TW) .................................. 107126172

(51) Int. Cl.
| | |
|---|---|
| A61H 1/02 | (2006.01) |
| A61H 3/00 | (2006.01) |
| A63B 22/02 | (2006.01) |
| A61B 5/11 | (2006.01) |
| A61B 5/00 | (2006.01) |
| A61H 3/04 | (2006.01) |

(52) U.S. Cl.
CPC ............ *A61H 1/0262* (2013.01); *A61B 5/112* (2013.01); *A61B 5/1128* (2013.01); *A61B 5/4836* (2013.01); *A61H 3/008* (2013.01); *A61H 3/04* (2013.01); *A63B 22/02* (2013.01); *A61B 2505/09* (2013.01); *A61B 2562/0219* (2013.01); *A61H 2201/1207* (2013.01); *A61H 2201/163* (2013.01); *A61H 2201/5007* (2013.01); *A61H 2201/5061* (2013.01); *A61H 2201/5071* (2013.01); *A63B 2220/20* (2013.01)

(58) Field of Classification Search
CPC ...................................................... A61B 5/112
See application file for complete search history.

(56) References Cited

U.S. PATENT DOCUMENTS

| | | | | |
|---|---|---|---|---|
| 5,575,765 | A * | 11/1996 | Foster .................... | A61H 1/008 606/241 |
| 6,666,798 | B2 * | 12/2003 | Borsheim .............. | A63B 21/28 434/247 |

(Continued)

*Primary Examiner* — Samchuan C Yao
*Assistant Examiner* — Nathan M Le
(74) *Attorney, Agent, or Firm* — Muncy, Geissler, Olds & Lowe, P.C.

(57) ABSTRACT

A gait activity learning assistance system, and an application method thereof, includes a main body, at least one movement detecting module, a control module, at least one driving module and at least one dynamic measurement module. The system is able to guide and induce a user to learn gait autonomously by disposing at least one force-transmission unit on at least one limb position of the user, besides, the system is able to measure a dynamic change of the at least one force-transmission unit by the at least one dynamic measurement module while user receiving a gait assistance, and send them back to the control module immediately for a real-time analysis.

6 Claims, 8 Drawing Sheets

(56) References Cited

U.S. PATENT DOCUMENTS

| | | | |
|---|---|---|---|
| 2012/0197168 A1* | 8/2012 | Agrawal | A63B 21/4009 |
| | | | 602/19 |
| 2014/0213951 A1* | 7/2014 | Pietrusisnki | A61H 3/008 |
| | | | 602/23 |
| 2016/0166460 A1* | 6/2016 | Murphy | A63B 21/00178 |
| | | | 601/34 |
| 2017/0027803 A1* | 2/2017 | Agrawal | A61B 5/1122 |
| 2017/0311848 A1* | 11/2017 | Wu | A61B 5/112 |

\* cited by examiner

GAIT ACTIVITY LEARNING ASSISTANCE SYSTEM AND THE APPLICATION METHOD THEREOF

CROSS-REFERENCE TO RELATED APPLICATION

This application claims priority to Taiwan Application No. 107126172, filed on Jul. 27, 2018, the entire content of which is hereby incorporated by reference herein in its entirety.

FIELD OF THE INVENTION

The present invention relates to a gait activity learning assistance system and the application method thereof, in particular, relates to a gait activity learning assistance system for guiding users to learn the gait activity spontaneously to induce a Neuro Developmental Treatment for recovering user's gait ability, and the application method thereof.

BACKGROUND OF THE INVENTION

Physical medicine and rehabilitation is a branch of clinical medicine, which refers to the ability to help patients recover from injury through physical therapy behavior or functional treatment behavior to improve the patient's life. The injury may include a joint movement disorder or losing control of the movement of patients caused by cerebrovascular disease, central nervous system injury, diabetes, occupational injury or orthopedic surgery.

Among them, the cerebrovascular diseases affect the patient's body self-control ability severely. Taking the stroke as an example, according to the statistics number of the early years in the United States, there are about 300 cases of stroke per 100,000 people, also, the published report of American Heart Association in 2005, also shows that there are about 700,000 strokes in the United States each year, of which about 500,000 are new cases, and the rest are patients with recurrence of stroke. In a comprehensive researching report, it also shows that the incidence of stroke for people over 55 years old is about 4 to 6%. Plus, the aging population is a potential risk, so that the number of people with high risk of stroke is increasing. Thus, all the information points out that the need of rehabilitation all around the world is increasing but the manpower of rehabilitation is limited. Taking Taiwan as an example, the statistics shows that there are more than 100,000 people with rehabilitation needs, and each physical therapist needs to assist 20 patients to rehabilitate per day averagely.

At present, there are several effective methods of rehabilitation have been established for stroke patients. Among them, there is a Neuro Developmental Treatment (NDT) which focuses on neuroplasticity and drives the brain reconstructs the body self-control ability during a physical practice or experience through a re-education of neuromuscular function; therefore, NDT is clinically considered to improve the patient's mobility disorder more fundamentally. The NDT integrates various rehabilitation techniques, including support, induction, guidance and inhibition, etc. Under current NDT rehabilitation conditions, the physical therapist personally assists the patient by hand to give an appropriate auxiliary force of thrust, tension, resistance or support force which evaluated in the rehabilitation process immediately. The auxiliary force supports the patient's affected limb in need to make the patient complete the stride action successfully, and is continuously given by the physical therapist during the rehabilitation process. However, the rehabilitation method implemented by manpower will inevitably cause the physical burden of the physical therapist, and will further cause a decreasing number of patients which the physical therapist is affordable to treat on a daily.

Based on the considerations of the lack of rehabilitation manpower, semi-automatic or automatic rehabilitation aids are produced, for example, a mechanical exoskeleton is a common auxiliary device for rehabilitation. However, the mechanical exoskeleton still exists many shortcomings such as: (1) the mechanical exoskeleton mainly provides supporting force for the thigh, calf and sole of the patient. When the patient uses the mechanical exoskeleton, it can only be passively controlled but produce the effect of independent learning; (2) because of the setting position where the mechanical exoskeleton is applying the force to the patient, the patient can only perform motion imitation but achieve the purpose of guiding; (3) the force points where the mechanical exoskeleton applying provide no correct sensory input to the patient, so that it is impossible to simulate the training method of physical therapists in performing NDT; (4) the mechanical exoskeleton cannot immediately detect and analyze the gait and movement of the patient, so the auxiliary parameters for the patient cannot be adjusted in time according to the patient's movement.

To summarize the content above, the conventional technology is unable to achieve the goal which is inducing and guiding the patient to learn gait activity because of the limitation of device design, operation method and implementation method. Also, the conventional technology is unable to assist or replace physical therapists in performing NDT; therefore, it is still necessary to develop a novel device or a novel system to solve the problem in the clinic.

SUMMARY OF THE INVENTION

A primary object of the present application is to provide a gait activity learning assistance system. According to the design of the system, the gait activity learning assistance system comprises at least one force-transmission unit which is configured to be disposed on at least one limb position of a user to guide the user and induce the user's limb to swing or rotate. By driving the at least one limb position of the user, the user is guided to process a correct gait reaction.

Another object of the present application is to provide a gait activity learning assistance system. According to the design of the system, the gait activity learning assistance system comprises at least one dynamic measurement module, being connected to the at least one force-transmission unit, wherein the at least one dynamic measurement module measures a dynamic change of the at least one force-transmission unit and generates at least one dynamic characteristic data; the at least one dynamic characteristic data is sent to a control module in real-time; the control module received the at least one dynamic characteristic data and performs a motor algorithm synchronously so as to adjust force execution timing, a forcing strength, and a forcing duration time of the at least one force-transmission unit according to the user's gait activity result.

To achieve the aforesaid objects, the present application provides a gait activity learning assistance system, comprising: a main body, which is set up in the system; at least one movement detecting module set up in the system for detecting and recording the change in movement of a user's limb to obtain at least one movement characteristic data; a control module, which is disposed on the main body and communication connected to the at least one movement detecting module, wherein the control module receives the at least one movement characteristic data and generates a control signal by calculating the received the at least one movement characteristic data; at least one driving module, which is disposed on the main body and electrically connected to the control module, wherein the at least one driving module comprises a motor driver being electrically connected to the control module, a motor being electrically connected to the motor driver and at least one force-transmission unit being connected to the motor; the motor driver receives the control signal and turns the control signal into a motor driving signal; the motor receives the motor driving signal to generate a driving force correspondingly; the at least one force-transmission unit is configured to be disposed on at least one limb position of a user and receives the driving force to guide the user to generate a gait reaction and induce the user's limb to swing or rotate; at least one dynamic measurement module being connected to the at least one force-transmission unit and communication connected to the control module, wherein the at least one dynamic measurement module measures a dynamic change of the at least one force-transmission unit and generate at least one dynamic characteristic data; the at least one dynamic characteristic data is sent to the control module in real-time; and a moving assistant assembly, which is set up in the system and moves with the user's gait activity; wherein the control module receives the at least one dynamic characteristic data and performs a motor algorithm synchronously to generate a second control signal including a driving force execution timing signal of the motor, a force strength signal and a forcing duration information; the second control signal is sent to the motor driver to drive the motor, thereby generating a second driving force; the second driving force is received by the at least one force-transmission unit to configure to drive the at least one limb position of user which needs to be driven such that the user is guided to process a correct gait reaction.

According to an embodiment of the present application, the gait activity learning assistance system further comprises a wearing unit configured to keep the user in a state of standing posture.

According to an embodiment of the present application, the gait activity learning assistance system further comprises a supporting unit adapted to generate a supporting force for at least one lower limb of the user.

According to an embodiment of the present application, the at least one force-transmission unit is an elastic belt.

According to an embodiment of the present application, the at least one movement detecting module comprises an image capturing unit, a body motion tracking unit, a distance measurement unit, a distance scanning unit, an inertial measurement unit or a combination thereof.

According to an embodiment of the present application, the second control signal further comprises a displacement information of the at least one limb position.

According to an embodiment of the present application, the at least one movement characteristic data comprises stance phase duration, swing phase duration, double-limb support phase duration, the time of heel strike, the time of foot flat, the time of heel off, the time of toe off, foot strikes, hip angle, knee joint angle, hip joint position, ankle angle, number of steps per unit time, walking distance per unit time, step length of the healthy side, step length of the affected side, stride length, step width, foot angle, gait symmetry, change in balance, body alignment, base of support, ratio of the stance phase to the swing phase on the same side, ratio of the stance phase to the swing phase on the different sides, percentage of the time of each stage in stance phase, or any combinations thereof.

According to an embodiment of the present application, the at least one dynamic measurement module comprises a force measurement unit, a distance measurement unit, a distance scanning unit, an angle measurement unit, a pressure sensor unit, or any combinations thereof.

According to an embodiment of the present application, the at least one dynamic characteristic data comprises a forcing strength, a forcing duration and a forcing direction.

According to an embodiment of the present application, the control module comprises a receiving unit, a processing unit and a transmitting unit.

According to an embodiment of the present application, the receiving unit is adapted to receive the at least one movement characteristic data or the dynamic characteristic data; the processing unit is adapted to turn the at least one movement characteristic data or the dynamic characteristic data into the control signal or the second control signal by calculating the at least one movement characteristic data or the dynamic characteristic data; the transmitting unit is adapted to transmit the control signal or the second control signal to the motor driver.

According to an embodiment of the present application, the processing unit is adapted to perform a motor algorithm, wherein the motor algorithm comprises the steps of: setting up a default to the motor, wherein the default is an initial action force; verifying if a heel is on the ground; verifying if the location of the heel is in front of another heel; verifying if the heel is on the ground again; and generating a second control signal by the forgoing results.

According to an embodiment of the present application, the motor driving signal is a voltage signal, a current signal, a frequency signal, a pulse width signal, or any combinations thereof.

According to an embodiment of the present application, the at least one limb position is a pelvic region, a posterior sacral region, a distal segment of the limb, an abdomen, and any combinations thereof.

In additional, to achieve aforesaid objects, the present application provides an applicable method of the gait activity learning assistance system for guiding user to process a correct gait reaction and learn gait activity, including the following steps: disposing at least one force-transmission unit on at least one limb position of a user; detecting the change in user's limb by at least one movement detecting module to generate at least one movement characteristic data while the user is walking; generating a control signal by a control module which receives the at least one movement characteristic data and transmitting the control signal to a motor driver of at least one driving module; turning the control signal it into a motor driving signal by the motor driver and transmitting the motor driving signal to a motor to generate a driving force correspondingly; driving the at least one limb position of the user by the driving force of the motor to guide the user to process the gait reaction and induce the user's limb to swing or rotate; measuring the dynamic change of the at least one the force-transmission unit by the at least one dynamic measurement module to generate the at least one dynamic characteristic data; wherein the at least one dynamic characteristic data is sent to the control module in real-time; the control module received the at least one dynamic characteristic data and performs the motor algorithm synchronously to generate the second control signal, wherein the second control signal includes a driving force execution timing signal of the motor, a forcing strength signal, a forcing duration information, and a displacement information of the at least one limb position; and driving the at least one force-transmission unit via the motor driver and the motor according to the second control signal to drive the at least one limb position of the user to induce the user's limb to swing or rotate before processing the gait reaction so as to guide the user to process the correct gait reaction.

According to an embodiment of the present application, the steps of the motor algorithm comprises: setting up a default for the motor, wherein the default is an initial action force; verifying if a heel is on the ground; verifying if the location of the heel is in front of the other heel; verifying if the heel is on the ground again; and generating a second control signal by forgoing result.

In additional, to achieve the aforesaid objects, the present application provides an application method of a gait activity learning assistance system for simulating treatment of rehabilitation therapists and recording treatment record in the system as a personal assisting mode of gait activity learning, comprising steps of: disposing at least one force-transmission unit on at least one limb position of a user; providing a gait assistance which applied on the at least one limb position of the user while the user is walking; detecting a displacement of the user's limb by at least one movement detecting module when the user receives the gait assistance to generate and record at least one movement characteristic data, and measuring a dynamic change of the at least one force-transmission unit by at least one dynamic measurement module when the user receives the gait assistance to generate and record at least one dynamic characteristic data; repeating the providing step and the detecting step at least two cycles to obtain force information of the gait assistance including the at least one movement characteristic data and the at least one dynamic characteristic data; and saving the force information in the system to establish a gait activity learning instruction.

According to an embodiment of the present application, the gait assistance is a manual rehabilitation which is applied to the user by a physical therapist.

According to an embodiment of the present application, the manual rehabilitation is a thrust force, a tension force, a resistance force, a support force, a slap force or a touch force.

According to an embodiment of the present application, the manual rehabilitation is applied on a pelvic region, a posterior sacral region, a distal segment of the limb, an abdomen, and any combinations thereof.

DETAILED DESCRIPTION OF THE INVENTION

Definitions

Figure 1:
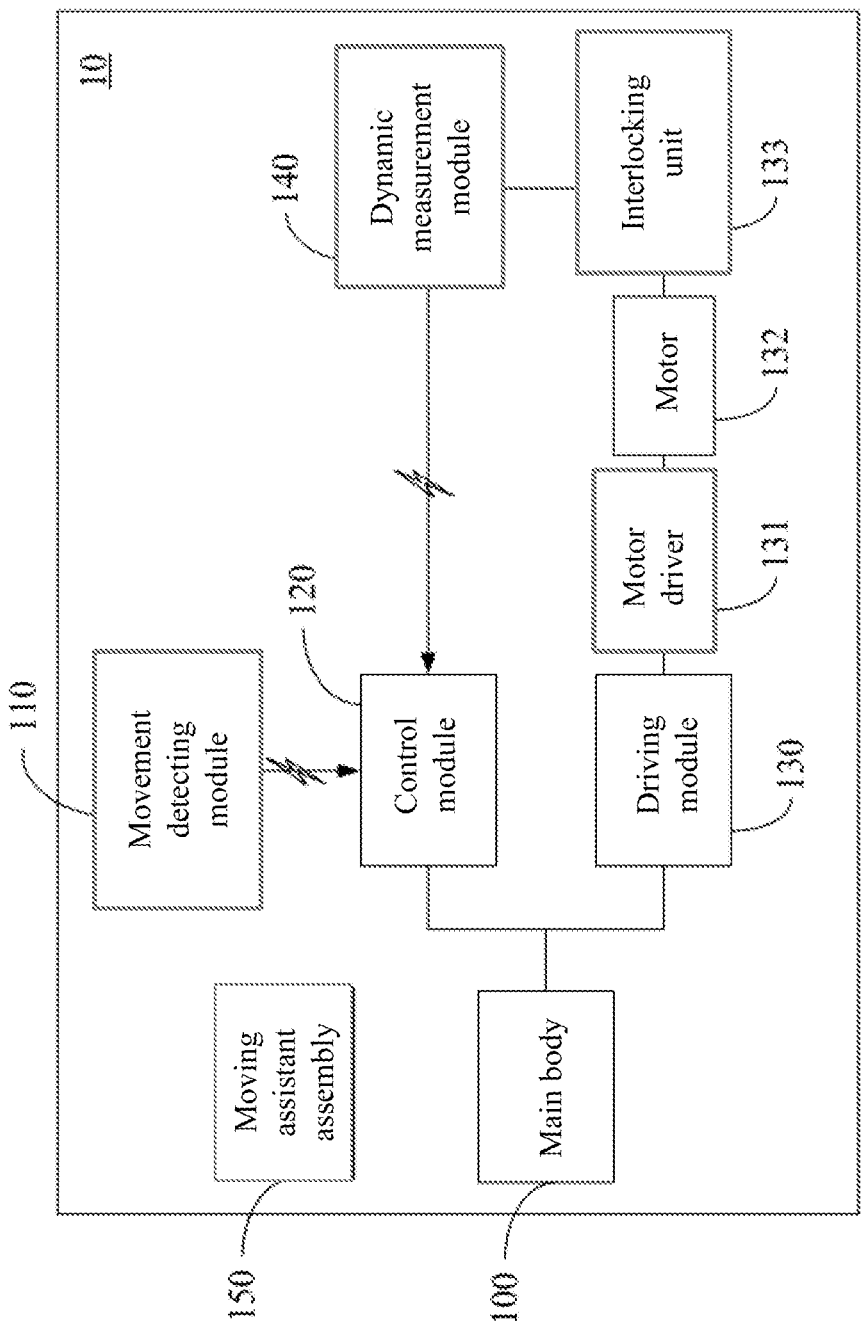
FIG. 1: a system block diagram of a preferred embodiment of the present application.

For helping the Examiner further realize and recognize the present application, some detailed descriptions and preferred embodiments are described as follows:

Given that the conventional gait activity assistance system has many insufficiencies and limitations, like the conventional gait activity assistance system cannot induce a user to have the effect of self-learning, or the user can only rely on the operation of the device to imitate the motion. Besides, the force points of the conventional gait activity assistance system provide the user with no correct sensory input, so that it is impossible to simulate the training method of physical therapists in performing NDT and adjust the auxiliary parameters for the user in time according to the user's movement. On these grounds, the present invention provides a gait activity learning assistance system and the application method thereof, it can (1) drive the user's limb to swing or rotate by a force-transmission unit to achieve the purpose of inducing or guiding the user to learn gait activity autonomously; (2) detect the change in user's limb movement and record the process of physical therapist performing NDT by a movement detecting module; (3) measure dynamic change in the force-transmission unit by a dynamic measurement module while user strides and send the change back to a control module immediately to process motor algorithm simultaneously, so the driving force execution timing signal of a motor, the forcing strength signal, the forcing duration information, the displacement information can be adjusted by user's need. Therefore, the present invention can mimic the rehabilitation strategy of physical therapist and provide a substitute way to replace the human resource of physical therapist in physical medicine and rehabilitation.

Therefore, the present invention provides a gait activity learning assistance system, including at least one movement detecting module which detects the change in movement of user's limb and obtains at least one movement characteristic data as a basis for the system to evaluate the state of user's gait; at least one control module that receives, analyzes and calculates at least one movement characteristic data to give a command for a driving module to induce the limb of user to swing or rotate to at least one site, so that user can be induced or guided to learn the gait activity spontaneously; and at least one dynamic measurement module, which is connected to at least one interlocking module, measures a dynamic change in the force-transmission unit while user strides and obtains at least one dynamic characteristic data which is sent back to the control module for processing motor algorithm, so that the control module can adjust the timing, forcing strength, forcing duration or driving site immediately to allow user to retrain the brain through somatic perception instead of simply mimicking the movement of standard process.

According to the above reasons, the following descriptions demonstrate the present invention comprising elements, features, and their combinations or communications.

First of all, refer to FIG. 1, a system block diagram of a preferred embodiment of the present invention is shown. In this embodiment of the present invention, the gait activity learning assistance system 10 includes the main body 100, the movement detecting module 110, the control module 120, the driving module 130, the dynamic measurement module 140, and the moving assistant assembly 150. The main body 100 and the movement detecting module 110 are set on any position of the system 10; the movement detecting module 110 detects the change in user's limb to generate a movement characteristic data (not shown in FIG. 1); the control module 120 is disposed on the main body 100 and connected to the movement detecting module 110 through communication, and generates a first control signal after analyzing and calculating the movement characteristic data received from the movement detecting module 110 (not shown in FIG. 1); the driving module 130, set on the main body 100 and electronically connected to the control module 120, comprising the motor driver 131, which receives the control signal generated by the control module 120 and turns the control signal into a motor driving signal (not shown in FIG. 1), the motor 132, which receives the motor driving signal and turns the motor driving signal into a driving force (not shown in FIG. 1), and the force-transmission unit 133, which is driven by the driving force; the dynamic measurement module 140, connected to the force-transmission unit 133 and linked to the control module 120 through communication at the same time, detects a dynamic change in the force-transmission unit 133 while user accepts the assistance from the system 10 and then generates a dynamic characteristic data (not shown in FIG. 1) which will be transmitted to the control module 120 immediately to process a motor algorithm to outcome a second control signal; the moving assistant assembly 150 is deposited on any position of the system 10, so that the system 10 is a movable system and will move with stride action of user.

As mentioned above, the movement detecting module detects the change in the user's limb and then analyzes the change to define to generate movement characteristic data. The movement detecting module is an optical sensing unit, an inertial sensing unit or a combination thereof. Therefore, the movement detecting module comprises an image capturing unit, a body motion tracking unit, a distance measurement unit, a distance scanning unit, an inertial measurement unit or a combination thereof, and the number of the movement detecting module in the system is in demand to be one or multiple. After the movement detecting module analyzes the change in the limb of the user, the movement characteristic data, including stance phase duration, swing phase duration, double-limb support phase duration, the time of heel strike, the time of foot flat, the time of heel off, the time of toe off, foot strikes, hip angle, knee joint angle, hip joint position, ankle angle, number of steps per unit time, walking distance per unit time, step length of the healthy side, step length of the affected side, stride length, step width, foot angle, gait symmetry, change in balance, body alignment, base of support, ratio of the stance phase to the swing phase on the same side, ratio of the stance phase to the swing phase on the different sides, percent of the time of each stage in stance phase, or any combinations thereof, is obtained. Thus, the movement detecting module is capable of analyzing any change in limb, and recording the change in the system as the movement characteristic data to establish a personal database of gait activity learning process. And furthermore, the movement characteristic data is sent back to the control module to provide the driving module with a suggestion of force timing and force strength.

Figure 2:
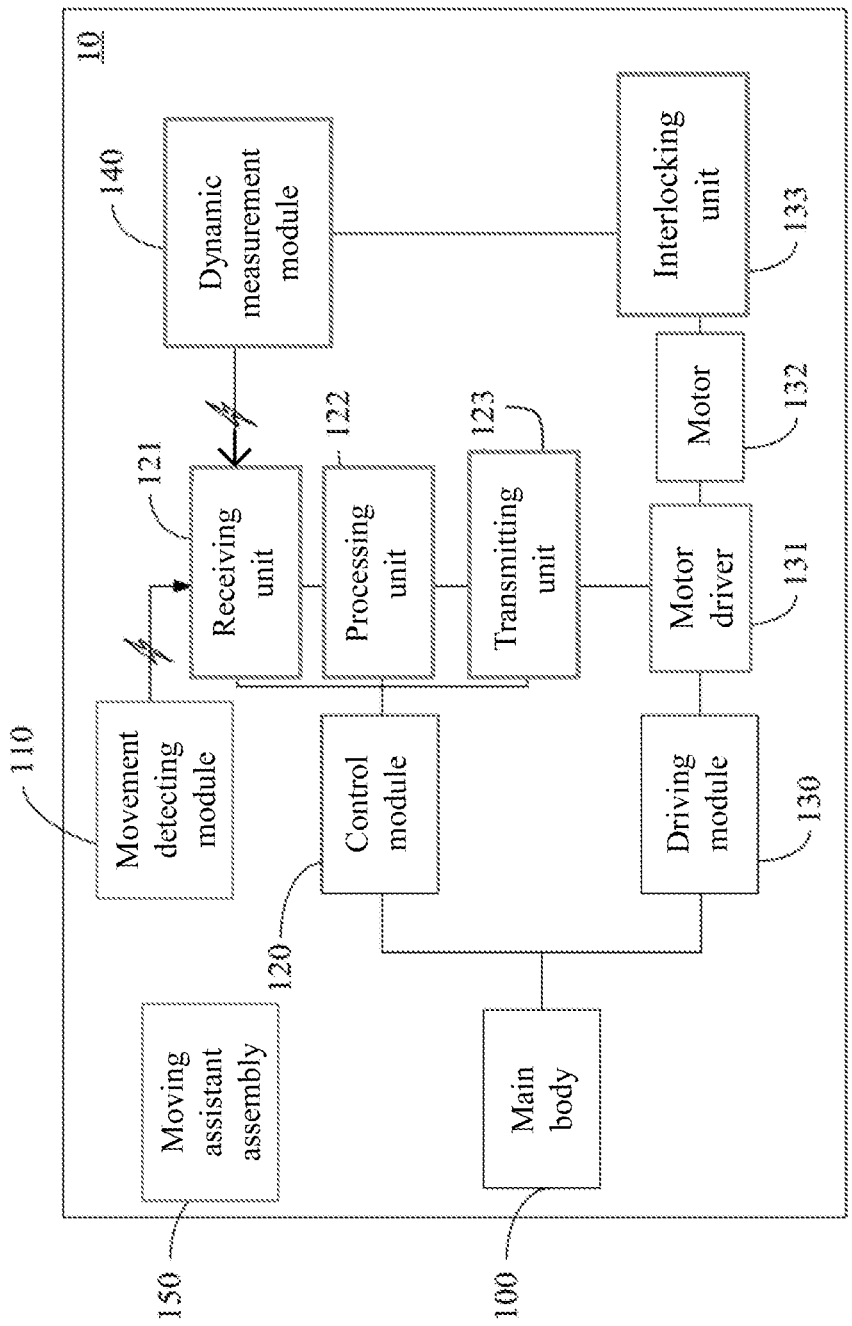
FIG. 2: a system block diagram of a preferred embodiment of the present application.

Refer to the FIG. 2, the system block diagram of one embodiment of the present invention is shown. In this embodiment of the present invention, the control module 120 of the gait activity learning assistance system 10 comprises the receiving unit 121, the processing unit 122 and the transmitting unit 123. The receiving unit 121 receives movement characteristic data from the movement detecting module 110 or dynamic characteristic data from the dynamic measurement module 140 and the processing unit 122 calculates those data to obtain a control signal and a second control signal respectively. The transmitting unit 123 sends those 2 kinds of control signals to the motor driver 131 of the driving module 130. And the motor driver 131 turns 2 kinds of the control signals into motor driving signals to drive the motor 132, so that this signal path can be executed in loop.

Back to FIG. 1, the driving module is set for receiving the control signal from the control module, and then the motor driver of the driving module drives the motor to move the force-transmission unit to guide the user. The number of the driving motor is in demand to be one or multiple. Furthermore, the motor driver is a device that is capable of providing a suitable driving signal to drive the motor. The driving signal comprises a voltage, a current, a frequency or a wave width, but it's not limited to those above kinds. The motor driver can be a general motor driver as everyone knows, like an electric motor driver. And the motor, an electric motor, an electric linear motor or a stepping motor, is picked in corresponding with the chosen motor driver, so it's not limited either.

Besides, the force-transmission unit is disposed on at least one limb position where is able to induce the user's limb to swing or rotate, so that the force-transmission unit has to possess enough structural strength and elasticity to support the user and provide a buffer to ease the uncomfortableness, and to be able to swing or rotate with the user while the motor drives. According to the above reasons, the force-transmission unit can be an elastic belt, but it's an alternative.

In one embodiment of the present invention, the number of the force-transmission unit depends on how many limb positions are considered to allow the user's limb to swing or rotate. The limb position comprises a pelvic region, a posterior sacral region, a distal segment of the limb, muscles of the abdomen and any combinations thereof. The force-transmission unit provides pelvic region or posterior sacral region with a forward force on the tangent direction of the pelvic region to drive the pelvic region or posterior sacral region to move forward or rotate. In addition, if the force-transmission unit forces on the distal segment of the limb, the upper limb or the lower limb of the user is guided to swing autonomously because the distal segment of the limb has a longer arm of force from joint. Furthermore, if the force-transmission unit forces on muscles of the abdomen, the muscles of the user are stimulated to contract. Hence, when the user rotates limb, swings limb, contracts muscle or any combinations thereof, the user is motivated or induced to control the lower limb autonomously to correspond with the system to give a response through perception. By the force-transmission unit of the system to guide the user continuously, the purpose of relearning to control muscle and limb is achieved to help elevate the therapeutic effect of neurodevelopment.

Also, refer to FIG. 1, the dynamic measurement module of the gait activity learning assistance system is connected to the force-transmission unit of the driving module, so that the dynamic measurement module is allowed to measure the dynamic change in the force-transmission unit while the force-transmission unit drives user. The dynamic measurement module is an optical sensing unit or a force sensing unit, and the number of it is in demand to be one or multiple. Therefore, the dynamic measurement module comprises a force measurement unit a distance detection unit, a distance scanning unit, an angle measurement unit, a pressure sensor unit or any combinations thereof. And the dynamic characteristic signal generated by the dynamic measurement module comprises a forcing strength, a forcing duration, a forcing direction or any combinations thereof.

Figure 3:
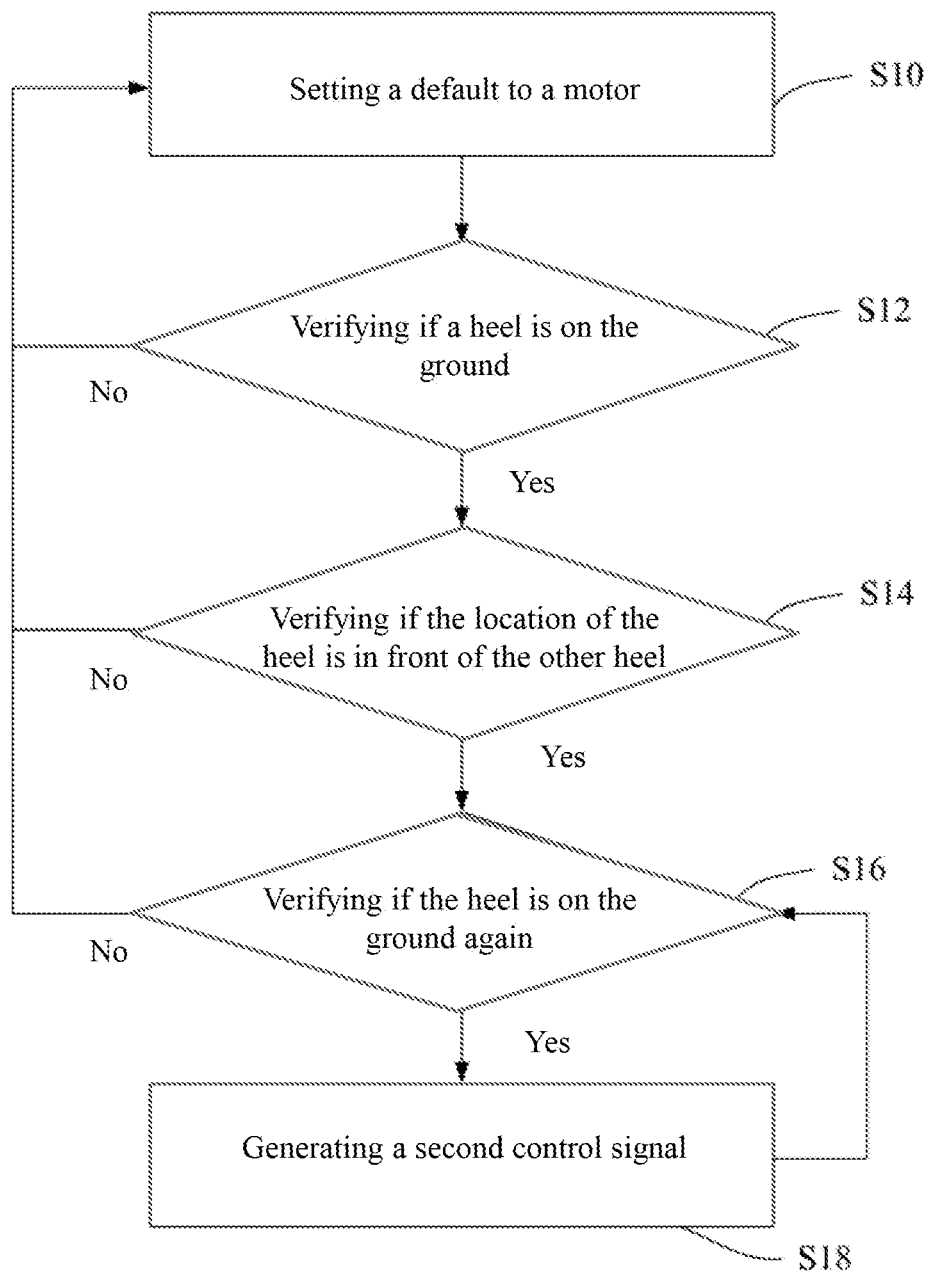
FIG. 3: a process diagram of a motor algorithm of a preferred embodiment of the present application.

The dynamic change in the force-transmission unit, comprising the forcing strength, the position, the duration while the force-transmission unit drives the user, is sent back to the control module immediately for analysis to obtain the dynamic characteristic data. Based on the dynamic characteristic data, the motor algorithm is processed to generate the second control signal. In one embodiment of the present invention, a process diagram of the motor algorithm, as shown in FIG. 3, for controlling the motor is illustrated as below:

Step S10: setting up a default to a motor;
Step S12: verifying if a heel is on the ground;
Step S14: verifying if the location of the heel is in front of the other heel;
Step S16: verifying if the heel is on the ground again;
Step S18: generate a second control signal.

In the step S10 of the above process, the default is an initial action force that does not move the at least one force-transmission unit. In one preferred embodiment of the present invention, the default is 0.5 to 1.5 lb. In the step S12, the processing unit verifies if the heel is on the ground. If the heel is off the ground, the motor will stay to provide the default only. On the contrary, if the heel is on the ground, another verification, the step S14, will be processed to verify whether the location of the heel is in front of the other heel or not. Likewise, if the location of the heel is behind the other heel, the motor will stay to provide the default. In contrast, if the location of the heel is in front of the other heel, the other verification, the step S16, will be processed to verify whether the heel is on the ground again or not. If the heel is off the ground, the motor will go back to provide the default to avoid over exerting on the user. If the heel is on the ground, a second control signal will be generated, as the step S18 indicates, to the motor driver of the driving module for driving the motor continuously.

The second control signal comprises a driving force execution timing signal of the motor, a forcing strength signal, a forcing duration information, a displacement information of the at least one limb position or any combinations thereof. In one preferred embodiment of the present invention, the trajectory value range of the driving force from the motor is between 0.5 to 6 lb to drive the force-transmission unit, so that the pelvic region, the posterior sacral region, the distal segment of the limb, the muscles of the abdomen or any combinations thereof of user is moved along with the force-transmission unit. Therefore, through detecting the dynamic change in the force-transmission unit by the dynamic measurement module, the timing, the force strength and the duration of the force-transmission unit while drives user are adjusted accurately. Also, the displacement of the limb position can be adjusted to increase or decrease, so that it can be decided to drive which body parts. By reproducing the rehabilitation assistance from a physical therapist by the system, the user can be guided to perform the gait activity accurately at the right timing and avoid to be over exerted. And the system provides the user with more accurate sensory input to elevate the effect of learning the gait activity autonomously and to achieve the purpose of therapeutic effect in neurodevelopment.

In FIG. 1, the purpose of setting up a moving assistant assembly is to provide a movable assistance system that moves along with the user while the user operates the assistance system. The moving assistant assembly is disposed on the system in roller or slide type, but it is not limited to only these two types. To be more detailed, if the moving assistant assembly is disposed in roller type, a wheeling device is set underneath the user or the main body. In the other case, a slide is set at any location in a particular space, and the slide and the main body are connected by a rope to attain the goal of being movable.

Figure 4:
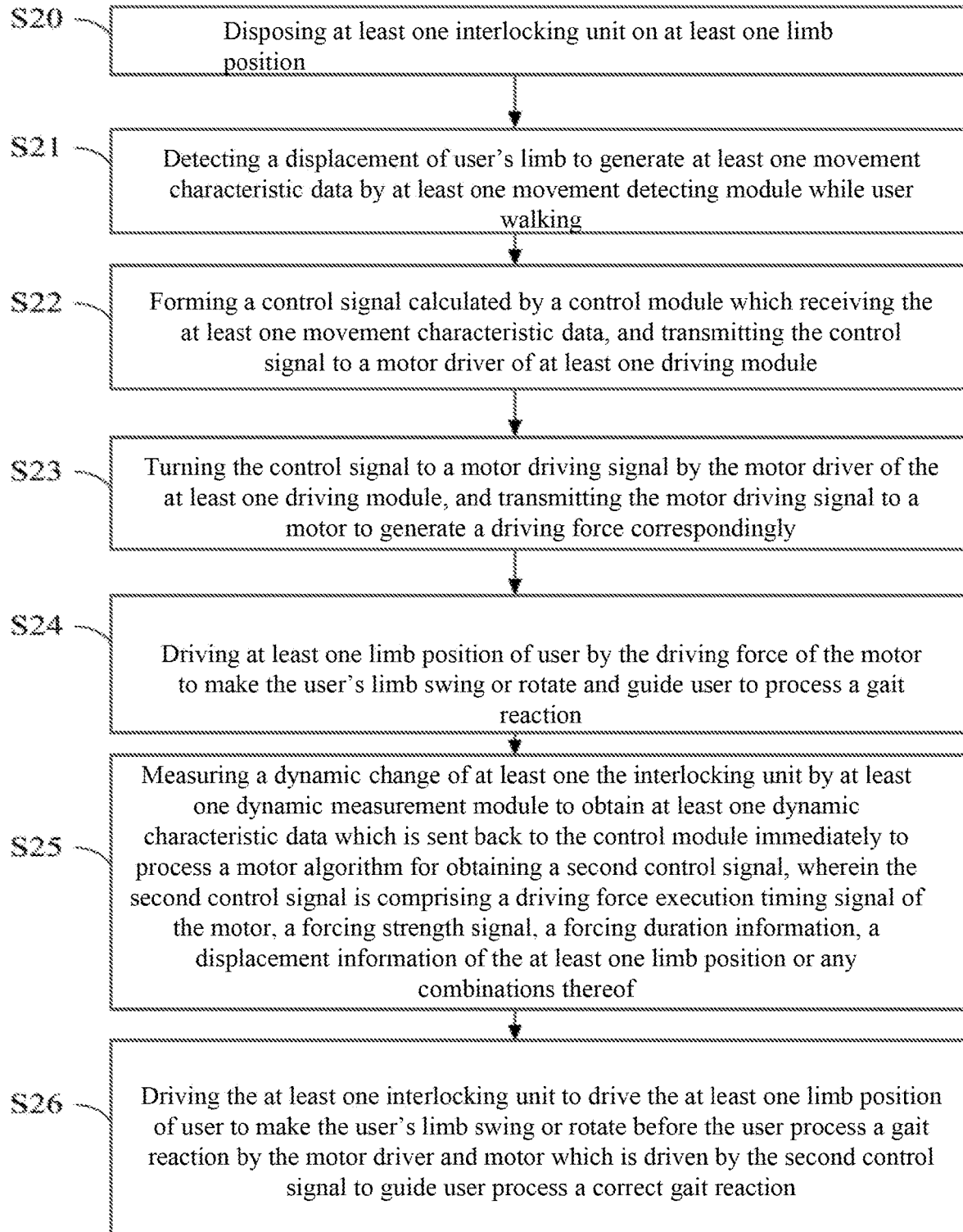
FIG. 4: a flow chart of a preferred embodiment of the application method of the present application.

Aforesaid gait activity learning assistance system is personalized by the following applications to attain the therapeutic effect in neurodevelopment:

Refer to FIG. 4, the flow chart of the application in one embodiment of the present invention, the step as below:

Step S20: disposing at least one force-transmission unit on at least one limb position;
Step S21: detecting a displacement of the user's limb to generate at least one movement characteristic data by at least one movement detecting module while the user walking;
Step S22: forming a control signal calculated by a control module which receiving the at least one movement characteristic data, and transmitting the control signal to a motor driver of at least one driving module;
Step S23: turning the control signal to a motor driving signal by the motor driver of the at least one driving module, and transmitting the motor driving signal to a motor to generate a driving force correspondingly;
Step S24: driving at least one limb position of a user by the driving force of the motor to guide the user to process a gait reaction and induce the user's limb to swing or rotate;
Step S25: measuring a dynamic change of at least one the force-transmission unit by at least one dynamic measurement module to obtain at least one dynamic characteristic data which is sent back to the control module immediately to process a motor algorithm for obtaining a second control signal, wherein the second control signal is comprising a driving force execution timing signal of the motor, a forcing strength signal, a forcing duration information, a displacement information of the at least one limb position or any combinations thereof;
Step S26: driving the at least one force-transmission unit to drive the at least one limb position of the user to induce the user's limb to swing or rotate before the user process a gait reaction by the motor driver and motor which is driven by the second control signal to guide user process a correct gait reaction.

In this embodiment of the present invention, as the step S20, the user can put the force-transmission unit on the key point body part, like the pelvic region, the posterior sacral region, the distal segment of the limb, the abdomen and any combinations thereof, to provide a right action force that allows limb to swing or rotate. The force-transmission unit is an elastic belt, and it provides pelvic region or posterior sacral region with a forward force on the tangent direction of the pelvis to drive the pelvic region or the posterior sacral region to move forward or rotate. In addition, if the force-transmission unit forces on the distal segment of the limb, the upper limb or the lower limb of the user is guided to swing autonomously because the distal segment of the limb has a longer arm of force from joint. Furthermore, if the force-transmission unit forces on the abdomen, the muscles of the user are stimulated to contract.

Next, as the step S21, the movement detecting module, an optical sensing unit or an inertial sensing unit, detects the change in the user's limb while the user operates stride action, and then analyzes the change to define and generate a movement characteristic data. Therefore, the movement detecting module comprises an image capturing unit, a body motion tracking unit, a distance measurement unit, a distance scanning unit, an inertial measurement unit or a combination thereof in demand. After the movement detecting module analyzes the change in the limb of the user, the movement characteristic data including stance phase duration, swing phase duration, double-limb support phase duration, the time of heel strike, the time of foot flat, the time of heel off, the time of toe off, foot strikes, hip angle, knee joint angle, hip joint position, ankle angle, number of steps per unit time, walking distance per unit time, step length of the healthy side, step length of the affected side, stride length, step width, foot angle, gait symmetry, change in balance, body alignment, base of support, ratio of the stance phase to the swing phase on the same side, ratio of the stance phase to the swing phase on the different sides, percentage of the time of each stage in stance phase, or any combinations thereof is obtained.

And as step S22 to S24 indicating, the control module receives and analyzes at least one movement characteristic data to generate the control signal which is sent to the motor driver of the driving module. The motor driver receives the control signal and turns it into the motor driving signal, sent to a motor to generate the driving force to drive the force-transmission unit, and the force-transmission unit moves the user at least one limb position to induce the user to swing, rotate, or contract, so that user can be induced to operate stride action.

As step S25, while user operates stride action, the at least one dynamic measurement module measures the dynamic change in the at least one force-transmission unit immediately and then generates at least one dynamic characteristic data which is sent back to the control module for processing motor algorithm, so that the force condition of the force-transmission unit, like execution time, force strength, force duration, can be adjusted according to the condition of the user's gait activity. In this way, the user is protected from being over exerted by the force-transmission unit and induced to control the limb for corresponding action autonomously by perception and cognition. Briefly, the system provides the user the sensory input and a cycling rehabilitation to meet the need, and induces the user to relearn the control of limb and muscle.

Figure 5:
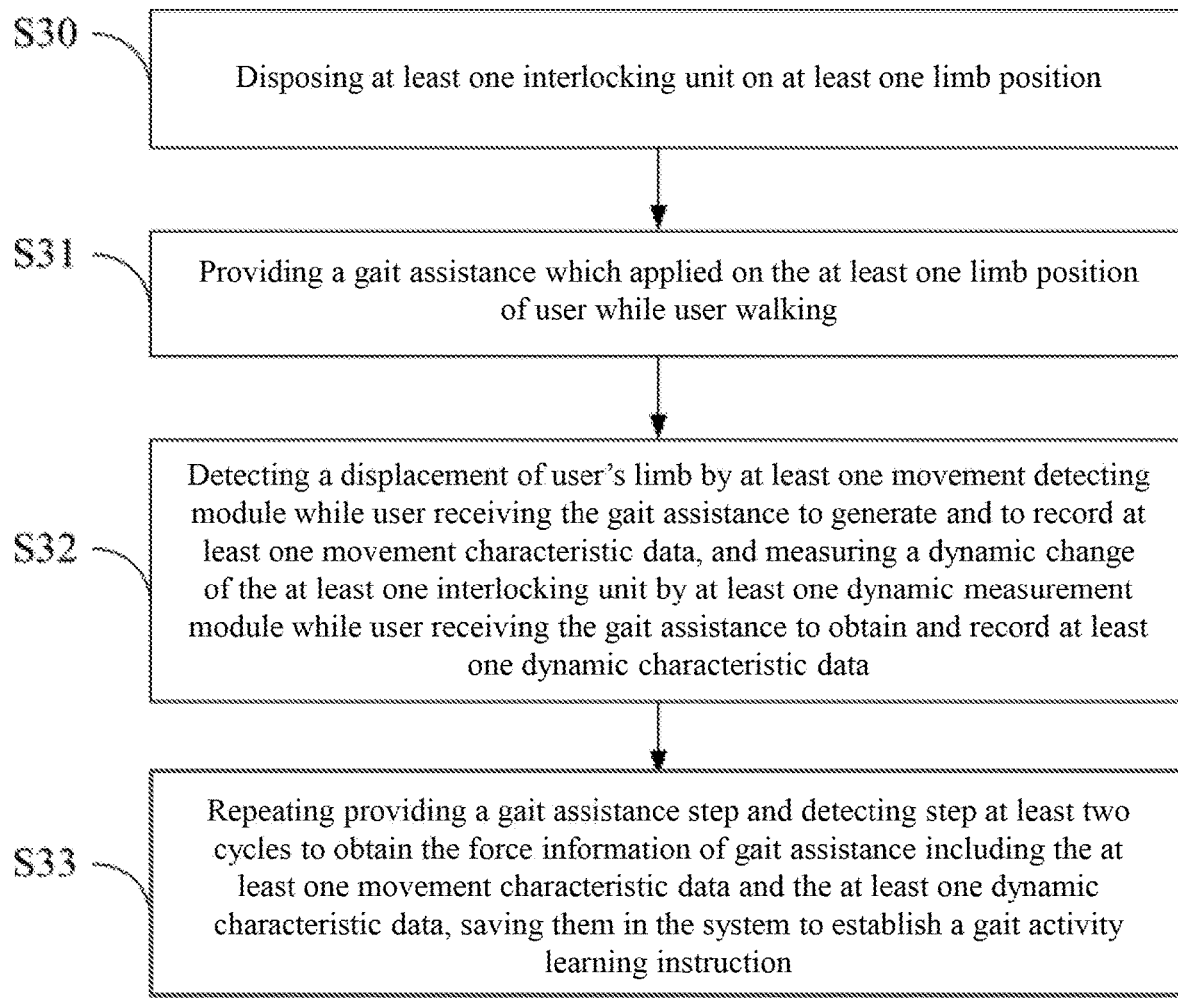
FIG. 5: a flow chart of a preferred embodiment of the application method of the present application.

Additionally, the system simulates the rehabilitation of physical therapists and records it in the system for repeating the same treatment to be a personal pad assisting mode of gait activity learning assistance. Refer to FIG. 5, a flow chart of one embodiment of the present invention shows the steps as follows:

Step S30: disposing at least one force-transmission unit on at least one limb position;

Step S31: providing a gait assistance which applied on the at least one limb position of the user while the user walking;

Step S32: detecting a displacement of the user's limb by at least one movement detecting module while the user receives the gait assistance to generate and to record at least one movement characteristic data, and measuring a dynamic change of the at least one force-transmission unit by at least one dynamic measurement module while user receiving the gait assistance to obtain and record at least one dynamic characteristic data;

Step S33: repeating providing a gait assistance step and detecting step at least two cycles to obtain the force information of gait assistance including the at least one movement characteristic data and the at least one dynamic characteristic data, saving them in the system to establish a gait activity learning instruction.

In the step S30 and S31 of this embodiment, the gait activity assistance is for giving a right sensory stimulation on key point of limb at the right timing while the user walks. To achieve the therapeutic effect in neurodevelopment, the gait activity assistance guides the user to induce a movement or contract muscles for making a right gait activity. To be more precise, the gait activity assistance is the manual rehabilitation performed by physical therapists, comprising a thrust force, a tension force, a resistance force, a support force, a slap force or a touch force. And the manual rehabilitation is applied on the pelvic region, the posterior sacral region, the distal segment of the limb, the muscles of the abdomen and any combinations thereof. A dynamic change, which is strength, time or position, in the force-transmission unit is measured accurately by at least one dynamic measurement module because the force-transmission unit is connected to at least one dynamic measurement module and disposed on at least one limb position. In this way, the gait activity assistance detects and analyzes the change in limb and the force-transmission unit by the at least one movement detecting module and at least one dynamic measurement module respectively to define at least one movement characteristic data and dynamic characteristic data for developing a gait activity learning instructor. And the gait activity learning instructor is saved in the system to be processed in demand of the user for re-performing the manual rehabilitation of the physical therapists, so that it is a substitute or an assistant strategy for rehabilitation.

The present invention is further illustrated by the following examples, which are provided for the purpose of demonstration rather than limitation.

EXAMPLES

The other characteristics and advantages of the present invention will be further illustrated and described in the following examples. The examples described herein are using for illustrations, not for limitations of the invention.

Example 1. Movement Detecting Module

In one embodiment of the present invention, a movement detecting module is an image sensing device based on the principles of optics. The image sensing device is an active capturing system to paste the active photosphere on key points of the user's limb, which includes four sides of lumbar joint, left or right thigh, left or right calf, left or right ankle, left or right mid foot, or left or right heel. A movement detector (like VZ4000) detects any movements of the user's limb immediately, so that the movement detecting module is allowed to analyze these movements and define them as a movement characteristic data for saving as a record or sending back to the control module to operate gait activity learning.

Example 2. Suspended and Wheeled Gait Activity Learning Assistance System

Figure 6:
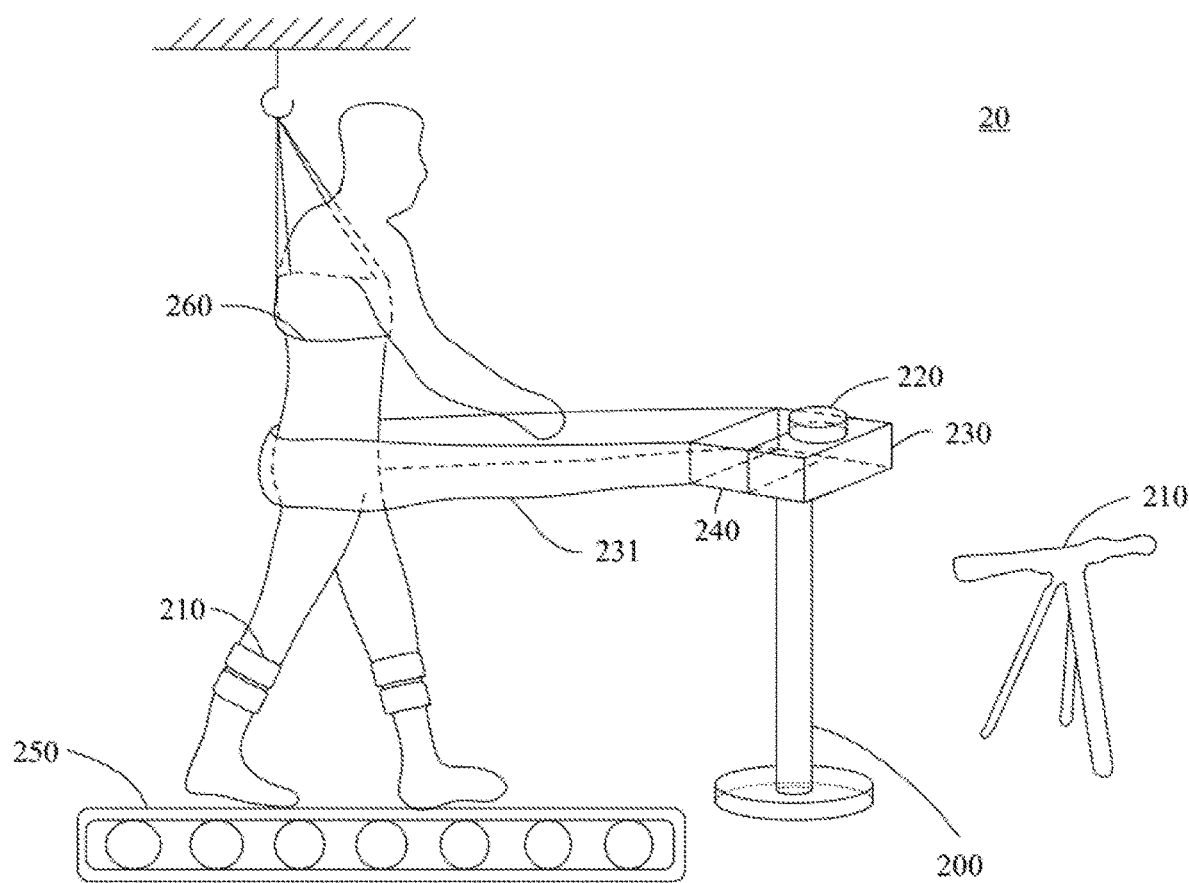
FIG. 6: a side view diagram of a preferred embodiment of the present application.

As shown in FIG. 6, it is a side view diagram of a preferred embodiment of present invention. The gait activity learning assistance system 20 comprises the main body 20, the at least one movement detecting module 210, the control module 220, the driving module 230, and the dynamic measurement module 240. The driving module 230 comprises a motor driver (not shown in FIG. 6), a motor (not shown in FIG. 6), and the elastic belt 231 which can be put on the user's pelvic region, posterior sacral region, distal segment of limb, abdomen, or any combinations thereof. In this embodiment of present invention, the elastic belt 231 supports the posterior sacral region and covers the pelvic region. The at least one movement detecting module 210 detects the change in the user's limb, so that the control module analyzes the change and generates movement characteristic data and a control signal. And the driving module is started to drive the elastic belt 231 for moving the user, so that the user's limb swings or rotates along with the elastic belt 231 to start gait reaction correspondingly. At the same time, the dynamic measurement module 240 measures the force strength, the duration and the change in position of the elastic belt 231 and sends these parameters back to the control module 220 for analyzing to generate dynamic characteristic data and a second control signal which comprises a driving force execution timing signal, a forcing strength signal, a forcing duration information, a displacement information of limb position and so on. In this way, while the user receives the assistance of the system, the driving force execution timing, the forcing strength, the forcing duration, and the displacement of limb position are adjusted instantly like a physical therapist depends on feedback of the user to adjust the condition of rehabilitation.

In this embodiment of the present invention, the gait activity learning assistance system 20 further comprises the moving assistant assembly 250 to reduce the resistance of stride for the user and the wearing unit 260 to provide a suspended supporting force as a protection from falling while the user is receiving the assistance of the system. Therefore, the assistance system is applicable for all different levels of impairment.

Example 3. Mobile Gait Activity Learning Assistance System

Figure 7:
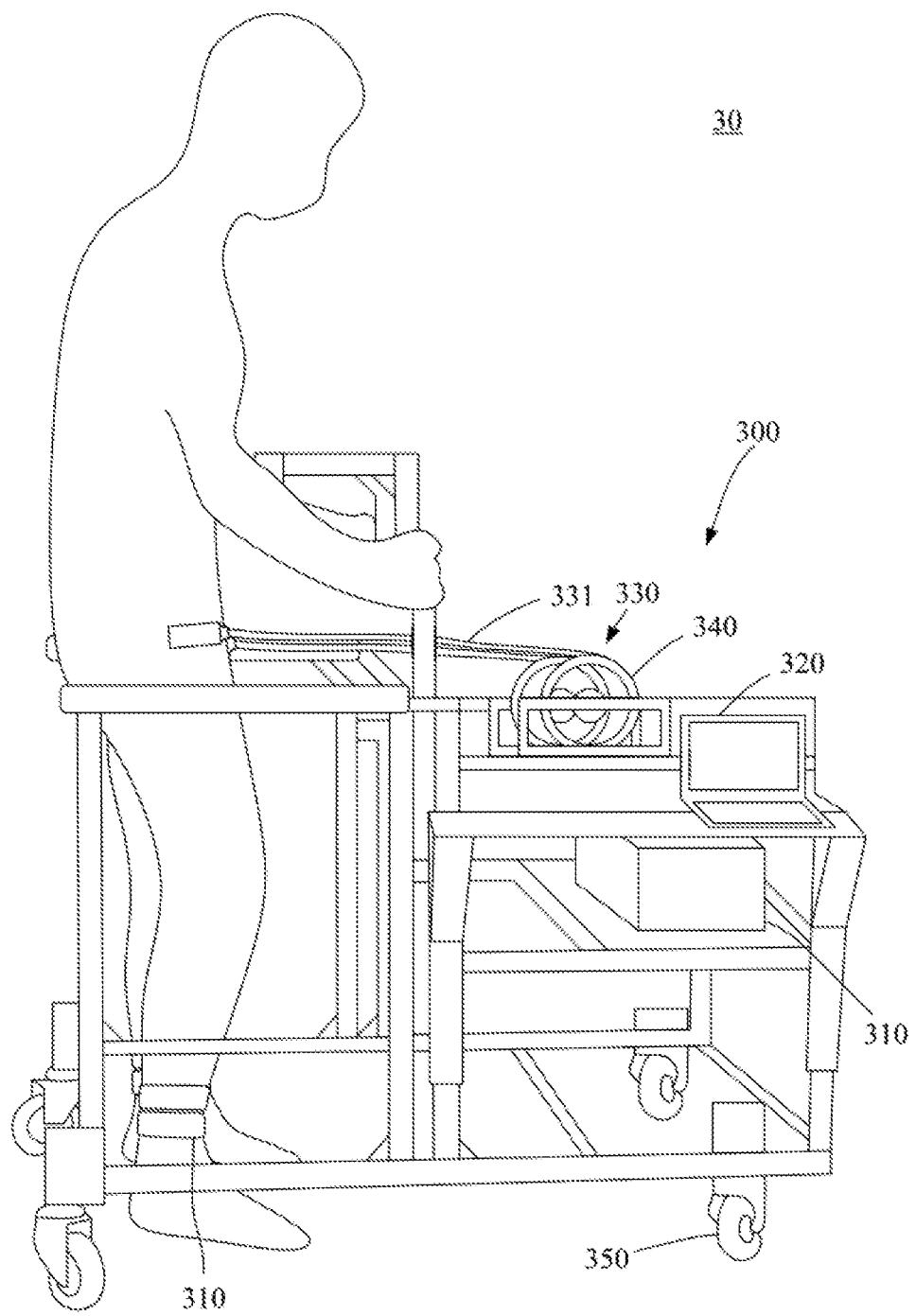
FIG. 7: a side view diagram of another view angle of a preferred embodiment of the present application.

In this embodiment of the present invention, as shown in FIG. 7, the gait activity learning assistance system 30, comprises the main body 300, the movement detecting module 310, the control module 320, the driving module 330, the dynamic measurement module 340, and the moving assistant assembly 350. The driving module 330 comprises a motor driver (not shown in FIG. 7), a motor (not shown in FIG. 7), and the force-transmission unit 331 which can be put on the user's waist, distal segment of limb, abdomen, or any combinations thereof. In this embodiment of the present invention, the force-transmission unit is put on the waist of the user to drive the waist to rotate and the body is moved along. The difference between this embodiment and Example 2 is the operational way of the moving assistant assembly 350. The moving assistant assembly 350 is wheels set underneath the main body 300 of the system 30, so that the system 30 is able to move along with the user to elevate the effect of learning gait activity autonomously. The rest of the operating principles are as same as Example 2.

Example 4. Suspended and Mobile Gait Activity Learning Assistance System

Figure 8:
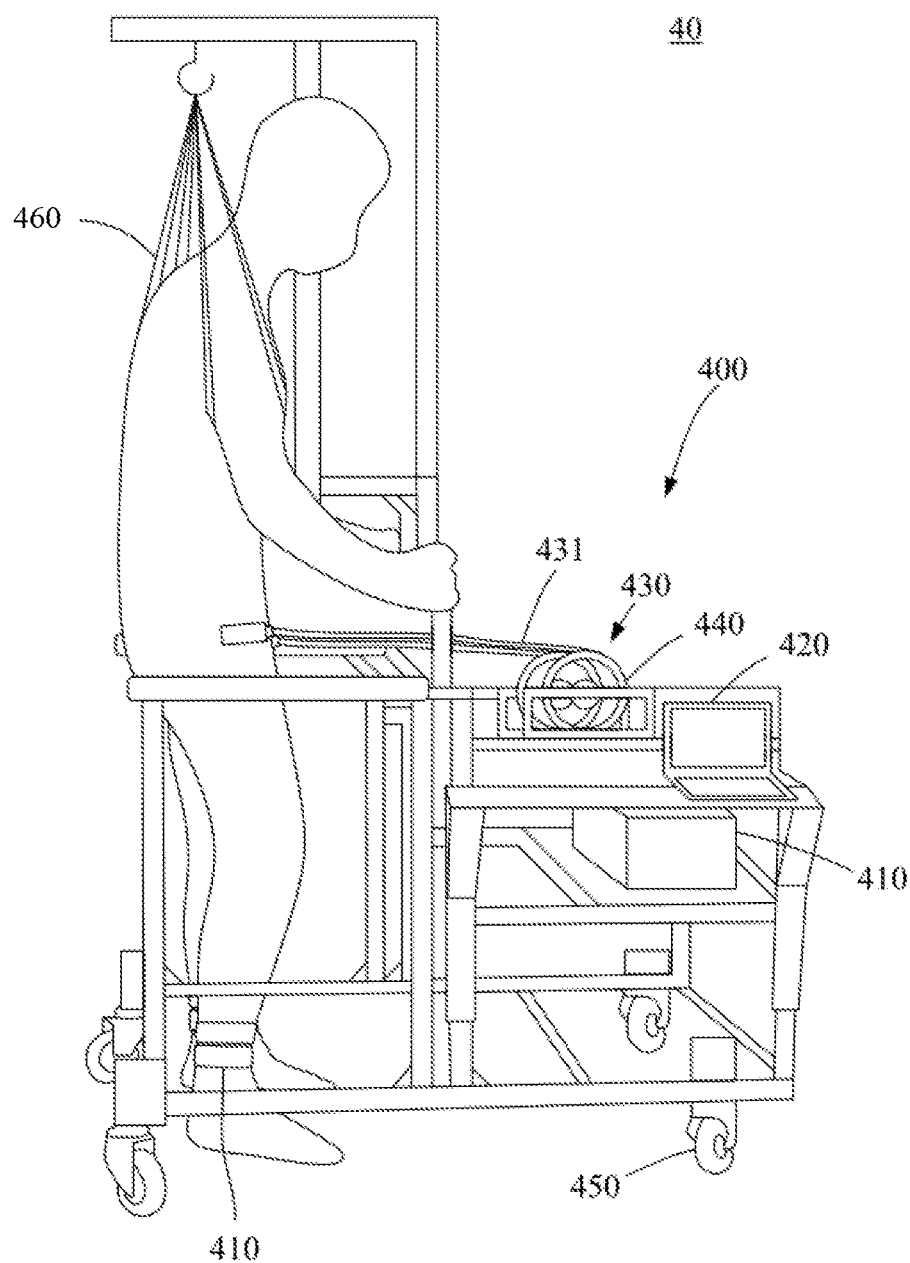
FIG. 8: a side view diagram of another preferred embodiment of the present application.

In this embodiment of the present invention, as shown in FIG. 8, most of the operating principles are as same as Example 2 and Example 3, the difference is this suspended and mobile gait activity learning assistance system further comprises the supporting unit 460. The supporting unit 460 provides a supporting force as protection from falling while the user is receiving the assistance of the system.

In summary of the above examples, the present invention is a gait activity learning assistance system to simulate the rehabilitation of physical therapists and re-perform it as an assistance or replacement of manual rehabilitation to reduce the loading of therapists by the at least one movement detecting module and the at least one force-transmission unit, which co-works with the dynamic measurement module and is deposed on the pelvic region, the posterior sacral region, the distal segment of the limb, the abdomen or any combinations thereof. And the at least one force-transmission unit forces on the pelvic region, the posterior sacral region, the distal segment of the limb or the abdomen to stimulate the nerves of these regions to guide the user to swing or rotate and induce the user to contract the muscles autonomously for operating stride action. With the help of cycling these actions, the user's brain is guided to relearn to control the muscles and stride to attain the purpose of the therapeutic effect of neurodevelopment. And the dynamic measurement module of the system detects the dynamic change in the at least one force-transmission unit and generates dynamic characteristic data to be send back to the control module. In this way, driving force execution timing, forcing strength, forcing duration, or forcing direction of the force-transmission unit on the user's pelvic region, posterior sacral region, distal segment of the limb, or the abdomen is adjusted immediately as parameters for protecting the user from being over exerted by the force-transmission unit and providing the user a more accurate sensor input to adjust the strength of the assistance. Therefore, the present invention provides a novel and feasible strategy and resolves the problem of clinical rehabilitation.

Although the present application has been explained above, it is not the limitation of the range, the sequence in practice, the material in practice, or the method in practice. Any modification or decoration for present application is not detached from the spirit and the range of such.

What is claimed is:

1. A method for guiding a user to process the correct gait reaction, comprising the steps of:
   providing a gait activity learning assistance system, comprising:
   a main body;
   at least one movement detecting module adapted for detecting and recording limb movement of a user to obtain at least one movement characteristic data;
   a control module disposed on the main body and communication connected to the at least one movement detecting module, wherein the control module receives the at least one movement characteristic data and outputs a control signal by calculating the received the at least one movement characteristic data;
   at least one driving module disposed on the main body and electrically connected to the control module, comprising:
   a motor driver electrically connected to the control module, wherein the motor driver receives the control signal and turns the control signal into a motor driving signal;
   a motor, electrically connected to the motor driver, wherein the motor receives the motor driving signal and generates a driving force correspondingly; and
   at least one force-transmission unit, being connected to the motor and configured to be disposed on at least one limb position, wherein the at least one force-transmission unit receives the driving force from the motor and is configured to drive the at least one limb position of the user to guide the user to process a gait reaction and induce the user to swing or rotate his/her limb;

at least one dynamic measurement module connected to the at least one force-transmission unit and communication connected to the control module, wherein the at least one dynamic measurement module measures a dynamic change of the at least one force-transmission unit and generates at least one dynamic characteristic data; the at least one dynamic characteristic data is sent to the control module in real-time; wherein the at least one force-transmission unit is an elastic belt configured to support the user's posterior sacral region and cover the user's pelvic region, said elastic belt being operational coupled to the at least one dynamic measurement module; wherein the dynamic measurement module further configured to measure the at least one dynamic characteristic data comprising a force strength, a duration and a change in position of the elastic belt; and a moving assistant assembly, which moves with the user's gait activity, wherein the control module received the at least one movement characteristic data and the at least one dynamic characteristic data and performs a motor algorithm synchronously to generate the control signal and a second control signal including a driving force execution timing signal of the motor, a forcing strength signal and a forcing duration information; the second control signal is sent to the motor driver to drive the motor, thereby generating a second driving force; the second driving force is received by the at least one force-transmission unit to configure to drive the at least one limb position of the user which needs to be driven such that the user is guided to process a correct gait reaction;

disposing the at least one force-transmission unit on the at least one limb position of the user;

detecting the displacement of the user's limb to generate the at least one movement characteristic data by the at least one movement detecting module while the user is walking;

generating the control signal calculated by the control module which receives the at least one movement characteristic data, and transmitting the control signal to the motor driver of the at least one driving module;

turning the control signal to the motor driving signal by the motor driver of the at least one driving module, and transmitting the motor driving signal to the motor to generate the driving force correspondingly;

driving the at least one limb position of the user by the driving force of the motor to guide the user to process the gait reaction and induce the user's limb to swing or rotate;

measuring the dynamic change of the at least one the force-transmission unit by the at least one dynamic measurement module to generate the at least one dynamic characteristic data, wherein the at least one dynamic characteristic data is sent to the control module in real-time; the control module received the at least one dynamic characteristic data and performs the motor algorithm synchronously to generate the second control signal, wherein the second control signal is comprising a driving force execution timing signal of the motor, a forcing strength signal, a forcing duration information, and a displacement information of the at least one limb position; and driving the at least one force-transmission unit via the motor driver and the motor according to the second control signal to drive the at least one limb position of the user to induce the user to swing or rotate his/her limb before processing the gait reaction so as to guide the user to process the correct gait reaction.

2. The method of claim 1, wherein the steps of performing the motor algorithm comprises:
setting up a default to the motor;
verifying if a heel is on the ground;
verifying if a location of the heel is in front of the other heel;
verifying if the heel is on the ground again; and
generating the second control signal.

3. A method for simulating treatment of rehabilitation therapists and recording treatment record as a personal assisting mode of gait activity learning, comprising steps of:
providing said gait activity learning assistance system of claim 1;
disposing the at least one force-transmission unit on the at least one limb position;
providing a gait assistance which applied on the at least one limb position of the user while the user is walking;
detecting a displacement of the user's limb by the at least one movement detecting module when the user receives the gait assistance to generate and record the at least one movement characteristic data, and measuring a dynamic change of the at least one force-transmission unit by the at least one dynamic measurement module when the user receives the gait assistance to generate and record the at least one dynamic characteristic data;
repeating the providing step and the detecting step at least two cycles to obtain force information of the gait assistance including the at least one movement characteristic data and the at least one dynamic characteristic data; and
saving the force information in the system to establish a gait activity learning instruction.

4. The method of claim 3, wherein the gait assistance is a manual rehabilitation which is applied to the user by a physical therapist.

5. The method of claim 4, wherein the manual rehabilitation is a thrust force, a tension force, a resistance force, a support force, a slap force or a touch force.

6. The method of claim 4, wherein the manual rehabilitation is applied on a pelvic region, a posterior sacral region, a distal segment of the limb, an abdomen or any combinations thereof.

* * * * *